United States Patent [19]

Berris

[11] Patent Number: 5,047,569

[45] Date of Patent: Sep. 10, 1991

[54] METHOD OF PRODUCING POLYSILANE COMPOUNDS

[75] Inventor: Bruce C. Berris, Baton Rouge, La.

[73] Assignee: Ethyl Corporation, Richmond, Va.

[21] Appl. No.: 548,483

[22] Filed: Jul. 3, 1990

[51] Int. Cl.$^5$ ................................................ C07F 7/08
[52] U.S. Cl. .................................... 556/430; 556/406
[58] Field of Search .............................. 556/430, 406

[56] References Cited

U.S. PATENT DOCUMENTS

| | | | |
|---|---|---|---|
| 4,578,495 | 3/1986 | Soula et al. | 556/430 X |
| 4,590,253 | 5/1986 | Hasegawa et al. | 556/430 X |
| 4,808,685 | 2/1989 | Bortolin | 556/430 X |

FOREIGN PATENT DOCUMENTS 0238826  9/1987  European Pat. Off. ............ 556/430

OTHER PUBLICATIONS

Gilman et al., "J. Organometal Chem.", 8, 1967, pp. 451–458.
"J.A.C.S.", 85, No. 7, 1963, p. 1016.

Primary Examiner—Paul F. Shaver
Attorney, Agent, or Firm—T. B. Morris

[57] ABSTRACT

Improved methods for producing polysilane compounds using diphosphorous nickel chloride catalysts.

15 Claims, No Drawings

METHOD OF PRODUCING POLYSILANE COMPOUNDS

This invention relates to methods of producing polysilane compounds by the polymerization of monomeric or oligomeric silane precusor material in the presence of nickel chloride catalysts.

BACKGROUND

Polysilane compounds have been produced heretofore by the reaction of dichlorosilane with metallic sodium. In these processes the silane has two R groups wherein R each represents hydrogen or hydrocarbon group, but not both R's are hydrogen at the same time. However, the method disadvantageously needs two moles of metallic sodium per mole of monomeric silane compound, and the use of metallic sodium in large amounts may not be feasible in the industrial production of polysilane compounds since, for example, sodium is readily combustible. Also, sodium tends to agglomerate during reactions, which can cause agitators to bind. The variability of sodium agglomerate size is difficult to control, causing product quality problems. Moreover, the thus produced polysilane compound tends to contain residual chloride ions which adversely affect the electrochemical properties of the polymer.

J. Am. Chem. Soc., 108, 4059 (1986) proposed a method in which a phenylsilane is polymerized in the presence of an organotitanium complex to produce an $(RSiH_2)_m(RSiH)_n$ compound wherein n is about six and m is 0 or 2.

J. Organometal Chem., 55 (1973), C7–C8, described the heating of a monomeric hydrosilane compound in the presence of an organorhodium complex, $(Ph_3P)_3RhCl$, which provides oligomers such as dimers or trimers of the hydrosilane together with a significant amount of disproportionation product. The disproportion product contaminates the desired polysilane compound and can not be readily removed from the polysilane compound.

U.S. Pat. No. 4,900,861 describes organocomplexes of nickel, cobalt, ruthenium, palladium and iridium effective as catalysts for the polymerization of a monomeric silane compound to produce higher molecular weight polysilane compound with substantially no byproducts of undesired disproportionation products.

There remains a need for improved methods of polymerizing silane and polysilane precursive material to produce polysilane compounds.

SUMMARY

Improved methods have now been discovered for producing polysilane compounds. These methods include the use of nickel chloride catalysts. The catalysts used provide increased activity requiring less catalyst. Additionally, they provide faster reactions. An additional benefit of the catalyst is its insolubility in the polysilane compound produced, thereby permitting relatively easy purification.

DESCRIPTION OF THE PREFERRED EMBODIMENTS

In one embodiment the present invention is a method for polymerizing a monomeric or polymeric silane precursor material to produce a polysilane compound. This method comprises polymerizing an appropriate monomeric or oligomeric silane precursor material in the presence of an effective amount of a nickel chloride catalyst producing a polysilane compound having an average molecular weight of about 500 or more. Unexpectedly the character of the nickel chloride catalyst provides enhanced activity and produces larger silane oligomers than previously attained.

The nickel catalysts used in the present invention are diphosphorous nickel halides. Preferred diphosphorous nickel halides are composed with two methyl groups attached to the phosphorous atom, e.g. dimethylalkylphosphine nickel halides. One such preferred catalyst is 1,2-bis(dimethylphosphino)ethanenickel (II) chloride, represented by the following formula:

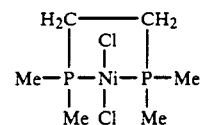

where Me is methyl-, P is phosphorous, Ni is nickel and Cl is chloride. Hereinafter, this preferred catalyst will alternatively be named "dmpe $NiCl_2$".

This preferred catalyst, dmpe $NiCl_2$, is reported in the literature, e.g. G. Booth & J. Chatt, "Some Complexes of Ditertiary Phosphorous with Ni(II) and Ni(III)", J. Chem. Soc., 3238 (1965). The catalyst can be a chloride, but need not be restricted to a chloride with bromides and iodide also usable, e.g. dmpe $NiBr_2$. Mixtures of halides may also be used. Likewise the alkyl linking chain need not be restricted to ethylene but can be any suitable alkyl group compatible with any solvent which might be present, e.g. a $C_1$ to about $C_6$ linear or branched group such as in 1,3-bis(dimethylphosphino)-propane nickel chloride. However, substitution of the hydrocarbon group, e.g. phenyl, in place of the methyl group reduces the activity of the resulting catalyst.

The dmpe $NiCl_2$ catalyst structure can have a tenfold increase in activity on a weight basis over other known catalysts such as monomeric $(Ph_3P)_3RhCl$ and $Cp_2ZrMe_2$ (where Me is methyl, Zr is zirconium and Cp is cyclopentadiene). The preferred catalyst can produce a nearly quantitative yield of products with molecular weights of at least about 500, preferably in the range of about 1000 to about 1500. Unexpectedly, recycled catalyst produced oligomer with higher molecular weight. Also, an induction period of several hours, with accompanying very slow reaction, was observed with fresh catalyst as compared to recycled catalyst.

In accordance with the invention, there is provided a method of producing a polysilane compound which comprises polymerizing a monomeric silane compound represented by the general formula

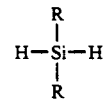

wherein R independently represents hydrogen or hydrocarbon group, but not both R's are hydrogen at the same time. When only one R is hydrogen, the compound can be represented by the formula $RSiH_3$.

Alternatively, an oligomeric compound can be used instead of the monomeric silane. The oligomeric silane compound used in the invention can be a polymeric silane precursor material, e.g. a silane polymer, which by example can be represented by the general formula

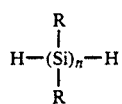

wherein R independently represents hydrogen or a hydrocarbon group, but not both R's are hydrogen at the same time, and n can range from about 2 to about 6. These precursor materials can be linear, branched or cyclic.

The product formed using either a monomeric or oligomeric silane precursor material can be either a linear, branched or cyclic polysilane. There need not be the same character of being linear, branched or cyclic for the precursive material as there is in the product, but there can be.

The R group for either monomeric or oligomeric silane units is a hydrocarbon group such that the silane unit is preferably either alkylsilane, arylsilane, dialkylsilane, diarylsilane or alkylarylsilane, in which the alkyl is preferably of one to about ten carbons and the aryl is preferably of about six to about fourteen carbons. More preferably the R group is phenyl, phenylalkyl (e.g., benzyl or phenethyl), alkylphenyl (e.g., tolyl or xylyl) or halophenyl (e.g. chlorophenyl or dichlorophenyl). The R group can be linear, branched or cyclic in structure, or a combination of such characters.

Thus, the monomeric silane compound used in the invention may be exemplified by alkylsilanes such as methylsilane, ethylsilane, n-propylsilane, isopropylsilane, n-butylsilane, n-pentylsilane, n-hexylsilane or n-heptylsilane; aryl silanes such as phenylsilane, benzylsilane or phenethylsilane; dialkylsilanes such as dimethylsilane, methylethylsilane, di-ethylsilane, methyl-n-propylsilane, methylisopropylsilane, ethyl-n-propylsilane, ethylisopropylsilane, diisopropylsilane, di-n-butylsilane or di-n-pentylsilane; alkylarylsilanes such as methylphenylsilane ethylphenylsilane: or diarylsilanes such as diphenylsilane, phenyl-o-tolylsilane, phenyl-p-tolylsilane, phenyl-m-tolylsilane, phenyl-p-chlorophenylsilane, phenyl-2,4-dimethylphenylsilane or phenyl-2,4-dichlorophenylsilane. The monomeric silane compound may be used singly or as a mixture of two or more of such monomeric silanes. Further, if desired, oligomers, preferably dimers or trimers, of the monomeric silane compounds may be used in place of the monomeric silanes or together therewith.

The preferred monomeric silane compound used in the invention is phenylsilane, methylphenylsilane, diphenylsilane, ethylphenylsilane or hexylsilane, with phenylsilane, methylphenylsilane or diphenylsilane most preferred. These characterizations of the R groups for the silane units apply to both reactants and product silanes.

One product produced by the present invention are linear structure polysilane compounds.

The linear structure polysilane compound may be represented by

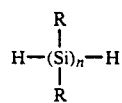

wherein R is the same as before, and n is an integer of not less than two, usually in the range of from two to about twenty. Preferably, n has a value of at least about ten.

Branched structure polysilane compounds can also be produced. When disubstituted silanes, e.g. diethylsilane or diphenylsilane are reacted in the presence of dmpe $NiCl_2$, the product is the dehydrodimer 1,1,2,2-tetraethyldisilane or 1,1,2,2-tetraphenylsilane, respectively.

The branched structure polysilane compounds have a silane branch through a Si-Si bond. An exemplified polysilane compound of the branched structure may be as follows:

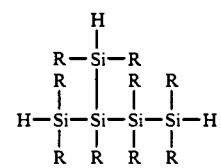

In addition to the linear or branched polysilanes, it is possible that cyclic polysilanes are produced. The cyclic structure polysilane compounds are represented by:

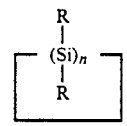

wherein R and n are as previously described.

In the method of the invention, the polymerization of the monomeric silane compound is carried out usually at temperatures in the range of from about $-20°$ C. to about 120° C., preferably from about 20° C. to about 50° C. The reaction time may be in the range of from about 10 minutes to about 2 days. The reaction time is preferably from about 1 hour to 1 day. These reaction times depend upon the reaction temperature employed. The higher the temperature, the less reaction time is required.

Usually the reaction is carried out in the absence of a solvent, but may be carried out in the presence of solvent, preferably inert to the reactants. The solvents include, for example, aromatic hydrocarbons such as benzene or toluene, ethers such as methyl ethyl ether, diethyl ether, tetrahydrofuran or dioxane, acid amides such as dimethylformamide, or acid esters such as ethyl acetate or butyl acetate.

The amount of catalyst employed in the reaction is usually from about 0.0001 mole to about 0.5 moles, preferably from about 0.001 moles to about 0.05 moles, per mole of the monomeric or oligomeric silane compound used.

It is desired that the reaction be carried out under an inert gas atmosphere such as nitrogen or argon. The progress of the reaction is confirmed by evolution of hydrogen gas from the reaction mixture.

According to the invention, the monomeric silane compound polymerizes readily in the presence of the catalyst to provide polysilane compounds in high yields with substantially no by-production of undesired disproportionation products. The catalyst used may be recovered from the reaction mixture, if desired.

The invention will now be described with reference to experimental examples which are, however, illustrative only and the invention is not limited to the examples.

DIMERIZATION OF DIPHENYLSILANE

A mixture of 25 mg of dmpe NiCl$_2$ and 5.0 gms of diphenylsilane was stirred magnetically in an open vial under an argon atmosphere in a glove box at room temperature for three days. The final product had solidified. 5 ml of reagent grade toluene were added to dissolve the product. The catalyst remained undissolved. The solution was filtered to remove the catalyst. The solution was then concentrated by subjection to a vacuum. 20 ml of ethanol were added, producing crystals. 3.35 gms of crystals were recovered, which had a tested melting point of 76.5°–77.5° C.

After an additional evaporation period from the mother liquor remaining, an additional 1.15 gms of crystals were recovered, which had a tested melting point of 75°–76.5° C. A total of 4.45 gms of crystal product was recovered, being a yield of 90.4%. Analysis of the crystals produced the following results:

| IR | $^1$H-NMR (d$_6$-Benzene) | $^{13}$C-NMR |
|---|---|---|
| 2120 cm$^{-1}$ | Δ 7.58 (m, 8H) | 128.42 |
| | 7.06 (m, 12H) | 129.71 |
| | 5.47 (s, 2H) | 132.75 (quat) |
| | | 136.37 |

This was compared with reported results of purified form of product in Bull. Soc. Chem. Fr., pg. 1548 (1974), which discloses melting point of 78°–79° C., $^1$H-NMR (CCl$_4$)Δ5.16 and an IR of 2108 cm$^{-1}$.

The following table provides the results of polymerizing the listed silane monomers using different nickel catalysts. Each experiment was performed by stirring 10 to 20 milligrams of catalyst together with 1 gram of the silane monomer in an open vial under argon for one to two days at room temperature.

| Catalyst | Silane Monomer | Product | Molecular Weight |
|---|---|---|---|
| NiCl$_2$ | hexyl | no reaction | — |
| (Ph$_3$P)$_2$Ni(CO)$_2$ | hexyl | no reaction | — |
| (Ph$_2$PCH$_2$—)$_2$NiCl$_2$ | hexyl | no reaction | — |
| dmpe NiCl$_2$* | hexyl | polysilane | 880 |
| recycled dmpe NiCl$_2$ | hexyl | polysilane | 960 |
| dmpe NiCl$_2$ | hexyl | polysilane | 950 |
| dmpe NiCl$_2$ | phenyl | polysilane | 590 |
| dmpe NiCl$_2$** | phenyl | polysilane | 510 |

*in 50% toluene
**in 50% toluene and at 105° C.

What is claimed is:

1. A method for polymerizing a monomeric or oligomeric silane precursor material to produce a polysilane compound comprising polymerizing said monomeric or polymeric silane precursor material in the presence of an effective amount of a diphosphorous nickel chloride catalyst for producing an average molecular weight of about 500 or more for said polysilane compound.

2. The method of claim 1 wherein the monomeric silane precursor is RSiH$_3$ and R is an alkyl, aryl, or alkylaryl group.

3. The method of claim 2 wherein said RSiH$_3$ is an alkylsilane.

4. The method of claim 3 wherein said alkylsilane has from one to about ten carbon atoms.

5. The method of claim 4 wherein the alkyl group of the alkylsilane is a linear alkyl.

6. The method of claim 5 wherein the linear alkyl group is methyl, ethyl or n-propyl.

7. The method of claim 2 wherein R of RSiH$_3$ is phenyl or methylphenyl.

8. The method of claim 1 wherein the monomeric silane precursor is R$_2$SiH$_2$, each R is independently either an alkyl, aryl or alkylaryl group, and the product is a dehydrodimer.

9. The method of claim 1 wherein said polysilane compound is linear.

10. The method of claim 1 wherein said polysilane compound has from about six to about twenty silicon atoms.

11. The method of claim 1 wherein said polysilane compound has at least ten silicon atoms.

12. The method of claim 11 wherein said average molecular weight is from at least about 1000 to about 2000.

13. The method of claim 1 wherein the diphosphorous nickel chloride catalyst comprises 1,2-bis(dimethylphosphino) ethanenickel (II) chloride.

14. The method of claim 13 wherein said polymerization is performed in a solvent.

15. The method of claim 14 wherein the solvent is toluene.

* * * * *